United States Patent [19] [11] 4,375,554
Fukui et al. [45] Mar. 1, 1983

[54] PROCESS FOR PREPARING AMIDINECARBOXYLIC ACIDS

[75] Inventors: Kiyoshi Fukui; Kiyomi Okimoto, both of Ichihara, Japan

[73] Assignee: UBE Industries Ltd., Ube, Japan

[21] Appl. No.: 318,598

[22] Filed: Nov. 5, 1981

[30] Foreign Application Priority Data

Nov. 18, 1980 [JP] Japan .................... 55/161386

[51] Int. Cl.³ .......................... C07C 119/00
[52] U.S. Cl. ...................... 562/440; 562/503; 562/507; 562/560
[58] Field of Search ........... 562/440, 560, 503, 507; 564/244, 225

[56] References Cited

U.S. PATENT DOCUMENTS 2,389,681 11/1945 Mikesha .................... 564/225
2,676,985  4/1954 Husted ...................... 564/225
3,538,139 11/1970 Hagemeyer et al. ......... 564/225
4,025,555  5/1977 Kraska et al. .............. 562/440

FOREIGN PATENT DOCUMENTS 44-5022018 7/1969 Japan .................... 562/5 60
50-83349    7/1975 Japan .................... 564/244

OTHER PUBLICATIONS

Gautier "The Preparation and Syn. Use of Amidines", pp. 292-307 (1975).
Sugiyama et al., J. Org. Chem., vol. 43, pp. 4485–4487 (1978).
Yashimura et al., Bull. Chem. Soc. Japan, vol. 44, pp. 3131-3136 (1971).

Primary Examiner—James H. Reamer
Attorney, Agent, or Firm—Frishauf, Holtz, Goodman & Woodward

[57] ABSTRACT

A process for preparing an amidinecarboxylic acid which comprises reacting, in water, an alkoxyiminoacetic acid ester represented by the formula

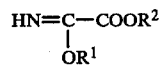

(wherein $R^1$ and $R^2$ individually represent an alkyl group of 1 to 4 carbon atoms) with an amine represented by the formula

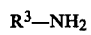

(wherein $R^3$ represents a hydrogen atom, an alkyl group of 1 to 4 carbon atoms, an alkenyl group of 2 to 4 carbon atoms, a cycloalkyl group of 5 to 7 carbon atoms or a benzyl group).

8 Claims, No Drawings

PROCESS FOR PREPARING AMIDINECARBOXYLIC ACIDS

This invention relates to a novel process for preparing amidinecarboxylic acids which are useful as an agricultural and horticultural fungicide.

It has been reported in the Bulletin of Chemical Society of Japan, 44, 3131 (1971) that the synthesis of amidinecarboxylic acids was attempted by the reaction of ethyl ethoxyiminoacetate with p-toluidine in a methanol solvent at room temperature for one hour, concentration of the resultant reaction mixture, treatment of the syrupy residue in 1 N hydrochloric acid at 65° C., and subsequent neutralization thereof with an alkaline compound, but there was not obtained the desired product at all.

It has also been disclosed in the Journal of Organic Chemistry, 43, 4485 (1978) that N-(p-tolyl)amidinecarboxylic acid was produced in a yield of 8% by the reaction of ethyl ethoxyiminoacetate with p-toluidine at 100° C. for 5 hours in the absence of a solvent, treatment of the reaction mixture with 6 N hydrochloric acid at 100° C. for 2 hours, and subsequent neutralization with potassium carbonate.

As seen from the foregoing, it is already known that the reaction of alkoxyiminoacetic acid esters with amines affords no or an extremely poor yield of amidinecarboxylic acids.

Then, the inventors of this invention have extensively studied in greater detail the reaction of an alkoxyiminoacetic acid ester with an amine and, as a result, found out that the reaction of both the materials first produces an amidinecarboxylic acid ester and then further reaction of the latter ester with an amine produces an amidinecarboxylic acid amide, and also that a high yield of the amidinecarboxylic acid will be obtained suppressing the secondary formation of the amidinecarboxylic acid amide if the amidinecarboxylic acid ester as produced is efficiently hydrolyzed in the reaction system.

This invention is based upon the above-mentioned viewpoint. More specifically, this invention is concerned with a process for preparing an amidinecarboxylic acid which comprises reacting, in water, an alkoxyiminoacetic acid ester represented by the formula

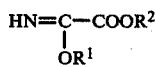  [I]

(wherein $R^1$ and $R^2$ individually represent an alkyl group of 1 to 4 carbon atoms) with an amine represented by the formula

  [II]

(wherein $R^3$ represents a hydrogen atom, an alkyl group of 1 to 4 carbon atoms, an alkenyl group of 2 to 4 carbon atoms, a cycloalkyl group of 5 to 7 carbon atoms or a benzyl group).

According to this invention, there can be obtained amidinecarboxylic acids in a high yield of 80% or even more, because the amidinecarboxylic acid ester produced in the reaction system can be rapidly hydrolyzed.

As illustrative examples of the alkoxyiminoacetic acid ester represented by the formula [I], there may be mentioned methyl methoxyiminoacetate, ethyl methoxyiminoacetate, butyl methoxyiminoacetate, methyl ethoxyiminoacetate, ethyl ethoxyiminoacetate, butyl ethoxyiminoacetate, propyl propoxyiminoacetate, butyl butoxyiminoacetate and the like.

As illustrative examples of the amine [II] represented by the formula [II], there may be mentioned ammonia, methylamine, ethylamine, propylamine, butylamine, allylamine, cyclopentylamine, cyclohexylamine, benzylamine, and the like. An amine and an alkoxyiminoacetic acid ester react in an equimolar amount, therefore both of them may generally be employed in an approximately equimolar amount.

The amount of water to be used is not critical, but it is preferably to be within 0.5~5 liters per mole of the alkoxyiminoacetic acid ester.

Reaction temperature is preferably within 0°~40° C. for preventing the starting alkoxyiminoacetic acid ester from hydrolyzing.

The reaction proceeds rapidly and comes to end usually in 1~3 hours.

The manner to conduct the reaction is not critical, but it is preferred to do the reaction by adding the amine or water containing the same to water containing the alkoxyiminoacetic acid ester.

Since the reaction proceeds almost stoichiometrically, the amidinecarboxylic acid as crystals can be recovered in a considerably high purity solely by concentrating the resultant reaction mixture. In a case, a small amount of some impurities may be included therein, then, the amidinecarboxylic acid can be isolated in a high purity by washing its concentrate with an organic solvent, generally, an alcohol or acetone, because being scarecely soluble in a usual organic solvent.

As illustrative examples of the amidinecarboxylic acids which can be obtained according to this invention, there may be mentioned amidinecarboxylic acid, N-methylamidinecarboxylic acid, N-ethylamidinecarboxylic acid, N-isopropylamidinecarboxylic acid, N-butylamidinecarboxylic acid, N-allylamidinecarboxylic acid, N-cyclohexylamidinecarboxylic acid, N-benzylamidinecarboxylic acid and the like.

Examples of this invention are given below.

EXAMPLE 1

To 20 ml of water containing 10.0 m mol of ethyl ethoxyiminoacetate were added 10 ml of water containing 10.7 m mol of ammonia and the reaction was carried out at room temperature for 4 hours.

The reaction mixture thus obtained was filtered to give 0.71 g (yield:81%) of amidinecarboxylic acid as crystals.

EXAMPLE 2

To 15 ml of water containing 10.0 m mol of ethyl ethoxyiminoacetate were added at room temperature 15 ml of water containing 10.1 m mol of methylamine and the reaction was carried out at room temperature for 17 hours.

The reaction mixture thus obtained was concentrated under reduced pressure to give 1.00 g (yield:98%) of N-methylamidine carboxylic acid as crystal, which was then recrystallized from methanol to give colorless block crystal with m.p. of 196°~197° C. (with decomposition). Its elementary analysis is as shown below.

|  | C | H | N |
|---|---|---|---|
| Found | 35.23 | 5.70 | 27.36 |

|  | C | H | N |
|---|---|---|---|
| Calc'd (for C₃H₆N₂O₂) | 35.29 | 5.93 | 27.44 |

EXAMPLE 3

Following the same procedures as in Example 2 except that 10.0 m mol of ethylamine were employed instead of the methylamine, there were obtained 1.15 g (yield:99%) of N-ethylamidine carboxylic acid as crystal. The crystal was recrystallized from ethanol to give colorless needles with m.p. 210°~211° C. (with decomposition). Its elementary analysis is as shown below.

|  | C | H | N |
|---|---|---|---|
| Found | 41.28 | 6.88 | 24.36 |
| Calc'd (for C₄H₈N₂O₂) | 41.38 | 6.94 | 24.12 |

EXAMPLE 4

Following the same procedures as in Example 2 except that 10.0 m mol of isopropylamine were employed instead of the methylamine, there were obtained 1.27 g (yield:98%) of N-isopropylamidine carboxylic acid as crystal. This crystal was recrystallized from ethanol to give colorless needles with m.p. 181°~182° C. (with decomposition). Its elementary analysis is as shown below.

|  | C | H | N |
|---|---|---|---|
| Found | 46.27 | 7.68 | 21.79 |
| Calc'd (for C₅H₁₀N₂O₂) | 46.15 | 7.74 | 21.52 |

EXAMPLE 5

To 20 ml of water containing 10.0 m mol (millimole) of ethyl ethoxyiminoacetate were added 10 ml of water containing 10.0 m mol of n-butylamine and then the reaction was carried out at room temperature for 4 hours.

The reaction mixture thus obtained was filtered to give 0.17 g (yield:12%) of N-n-butylmidinecarboxylic acid as crystal. The filtrate was concentrated under reduced pressure to additionally afford 1.25 g (yield:87%) of crystalline N-n-butylamidinecarboxylic acid. Both the crystals were combined and recrystallized from ethanol to give colorless block crystals with m.p. 179°~180° C. (with decomposition). Its elementary analysis is as shown below.

|  | C | H | N |
|---|---|---|---|
| Found | 49.68 | 8.07 | 19.57 |
| Calc'd (for C₆H₁₂N₂O₂) | 49.99 | 8.39 | 19.43 |

EXAMPLE 6

Following the same procedures as in Example 2 except that 10.0 m mol of allylamine were employed instead of the methylamine, there were obtained 1.23 g (yield:96%) of N-allylamidinecarboxylic acid as crystal. This crystal was recrystallized from ethanol to give colorless plates with m.p. 165°~166° C. (with decomposition). Its elementary analysis is as shown below.

|  | C | H | N |
|---|---|---|---|
| Found | 47.08 | 6.04 | 22.14 |
| Calc'd (for C₅H₈N₂O₂) | 46.87 | 6.29 | 21.86 |

EXAMPLE 7

To 15 ml of water containing 10.0 m mol of ethyl ethoxyiminoacetate were added at room temperature 15 ml of water containing 10.0 m mol of cyclohexylamine and the reaction was carried out at room temperature for one day.

The reaction mixture thus obtained was filtered to give 0.52 g (yield:31%) of crystalline N-cyclohexylamidinecarboxylic acid. The filtrate was concentrated under reduced pressure to additionally afford 1.17 g (yield:69%) of N-cyclohexylamidinecarboxylic acid as crystal. Both the crystals were combined and recrystallized from ethanol to give colorless needles with m.p. 168°~169° C. (with decomposition). Its elementary analysis is as shown below.

|  | C | H | N |
|---|---|---|---|
| Found | 56.63 | 7.97 | 16.70 |
| Calc'd (for C₈H₁₃N₂O₂) | 56.45 | 8.29 | 16.46 |

EXAMPLE 8

To 20 ml of water containing 10.0 m mol of ethyl ethoxyiminoacetate were added 10 ml of water containing 10.0 m mol of benzylamine at room temperature and the reaction was carried out at room temperature for 3 hours.

The reaction mixture thus obtained was filtered to give 1.39 g (yield:79%) of N-benzylamidinecarboxylic acid as crystal. The filtrate was concentrated under reduced pressure, the residual crystalline substance thus obtained was mixed with 5 ml of ethanol followed by filtration, thereby additionally affording 0.24 g (yield:13%) of N-benzylamidinecarboxylic acid as crystal. Both the crystals were combined and recrystallized from water to give colorless block crystals with m.p. 168°~169° C. (with decomposition). Its elementary analysis is as shown below.

|  | C | H | N |
|---|---|---|---|
| Found | 60.48 | 5.61 | 15.82 |
| Calc'd (for C₉H₁₀N₂O₂) | 60.67 | 5.66 | 15.72 |

COMPARATIVE EXAMPLE 1

To 30 ml of ethanol containing 10.0 m mol of ethyl ethoxyiminoacetate were added 10 m mol of benzylamine at room temperature and the reaction was carried out at room temperature for one day.

The reaction mixture thus obtained was filtered to give 0.42 g (yield:16%) of crystalline N-benzylamidinecarboxylic acid benzyl amide. The filtrate was concentrated under reduced pressure, 20 ml of water were added to the residue and hydrolysis was carried out at room temperature for one day. The mixture was filtered to yield a mixture of N-benzylamidinecarboxylic acid with its corresponding benzyl amide. The resulting mixture was added to 15 ml of acetone followed by filtration to give 0.21 g (yield:12%) of N-benzylamidinecarboxylic acid as crystal. The filtrate was concentrated to give 0.60 g (yield:22%) of N-benzylamidinecarboxylic acid benzyl amide as crystal.

The crystal of N-benzylamidinecarboxylic acid benzyl amide was recrystallized from ethanol to give colorless petal crystal with m.p. 145°–146° C. Its elementary analisis is as shown below.

|  | C | H | N |
|---|---|---|---|
| Found | 71.72 | 6.38 | 15.26 |
| Calc'd (for $C_{16}H_{17}N_3O$) | 71.89 | 6.41 | 15.72 | we claim:

1. A process for preparing an amidinecarboxylic acid which comprises reacting, in water, an alkoxyiminoacetic acid ester represented by the formula

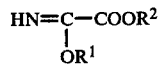

(wherein $R^1$ and $R^2$ individually represent an alkyl group of 1 to 4 carbon atoms) with an amine represented by the formula

(wherein $R^3$ represents a hydrogen atom, an alkyl group of 1 to 4 carbon atoms, an alkenyl group of 2 to 4 carbon atoms, a cycloalkyl group of 5 to 7 carbon atoms or a benzyl group).

2. A process for preparing an amidinecarboxylic acid according to claim 1, wherein said alkoxyiminoacetic acid ester is selected from the group consisting of methyl methoxyiminoacetate, ethyl methoxyiminoacetate, butyl methoxyiminoacetate, methyl ethoxyiminoacetate, ethyl ethoxyiminoacetate, butyl ethoxyiminoacetate, propyl propoxyiminoacetate, and butyl butoxyiminoacetate.

3. A process for preparing an amidinecarboxylic acid according to claim 1 or 2, wherein said amine is selected from the group consisting of ammonia, methylamine, ethylamine, propylamine, butylamine, allylamine, cyclopentylamine, cyclohexylamine, and benzylamine.

4. A process for preparing an amidinecarboxylic acid according to claim 1, wherein said reaction is carried out at a temperature of from 0° to 40° C. for 1 to 3 hours.

5. A process for preparing an amidinecarboxylic acid according to claim 1 or 4, wherein the amount of said water is within 0.5 to 5 liters per mole of the alkoxyiminoacetic acid ester.

6. A process for preparing an amidinecarboxylic acid according to claim 3, wherein said reaction is carried out at a temperature of from 0° to 40° C. for 1 to 3 hours.

7. A process for preparing an amidinecarboxylic acid according to claim 6, wherein the amount of said water is within 0.5 to 5 liters per mole of the alkoxyiminoacetic acid ester.

8. A process for preparing an amidinecarboxylic acid according to claim 3, wherein the amount of said water is within 0.5 to 5 liters per mole of the alkoxyiminoacetic acid ester.

* * * * *